United States Patent [19]

Riley et al.

[11] Patent Number: 4,552,145

[45] Date of Patent: Nov. 12, 1985

[54] NERVE IDENTIFICATION METHOD

[75] Inventors: Danny A. Riley, Brookfield, Wis.; James L. W. Bain, Sunnyvale, CA

[73] Assignee: The Medical College of Wisconsin, Milwaukee, Wis.

[21] Appl. No.: 508,854

[22] Filed: Jun. 29, 1983

[51] Int. Cl.$^4$ .............................................. A61N 5/00
[52] U.S. Cl. ........................................ 128/630; 435/4
[58] Field of Search ...................... 128/630; 435/4, 18, 435/19, 232, 805, 810

[56] References Cited

PUBLICATIONS

Sunderland, S.: The Anatomical Basis of Nerve Repair, in Nerve Repair and Regeneration, Ed. Jewett, D. L. and H. R. McCarroll, St. Louis, MO, C. V. Mosby, 1980, pp. 14–35.

Hakstian, R. W.: Funicular Orientation by Direct Stimulation: An Aid to Peripheral Nerve Repair, J. Bone Joint Surg., 50A:1178, 1968.

Gruber, H. and Zenker, W.: Acetylcholinesterase: Histochemical Differentiation Between Motor and Sensory Nerve Fibres, Brain Res. 51:207, 1973.

Gruber, H., Freilinger, G., Holle, J. and Mandl, H.: Identification of Motor and Sensory Funiculi in Cut Nerves and Their Selective Reunion, Brit. J. Plastic Surg. 29:70, 1976.

Riley, D. A., Ellis, S. and Bain, J.: Carbonic Anhydrase Histochemistry Reveals Subpopulations of Myelinated Axons in the Dorsal and Ventral Roots of Rat Spinal Nerves, Soc. for Neurosci., Abstr. 7:257, 1981.

Riley, D. A., Ellis, S. and Bain, J.: Carbonic Anhydrase Activity in Skeletal Muscle Fiber Types, Axons, Spindles, and Capillaries of Rat Soleus and Extensor Digitorum Muscles, J. Histochem. Cytochem. 30:1275, 1982.

Wong, V., Barrett, C. P., Donati, E. J., Eng, L. F. and Guth, L.: Carbonic Anhydrase Activity in First-Order Sensory Neurons of the Rat, J. Histochem. Cytochem. 31:293, 1983.

Riley, Danny A. and David H. Lang, 1983, Carbonic Anhydrase Activity of Human Peripheral Nerves, Anat. Rec. 205:162A–163A.

Riley, Danny A. and David H. Lang, 1983, Carbonic Anhydrase Activity of Human Peripheral Nerves, A Possible Histochemical Aid to Nerve Repair, J. Hand Surg. (In press).

Lonnerholm, G. 1980, Carbonic Anhydrase in Rat Liver and Rabbit Skeletal Muscle; Further Evidence for the Specificty of the Histochemical Cobalt–Phosphate Method of Hansson, J. Histochem. Cytochem. 28:427–433.

Millesi, H.: Interfascicular Nerve Repair and Secondary Repair with Nerve Grafts, in Nerve Repair and Regeneration, Ed. Jewett, D. L. and H. R. McCarroll, St. Louis, MO, C. V. Mosby, 1980, pp. 299–319.

Jabaley, M. E., Wallace, W. H. and Heckler, F. R.: Internal Topography of Major Nerves of the Forearm and Hand: A Current View, J. Hand Surg. 5:1, 1980.

Riley, D. A.: Ultrastructural Evidence for Axon Retraction During the Spontaneous Elimination of Polyneuronal Innervation of the Rat Soleus Muscle, J. Neurocytol. 10:425, 1981.

*Primary Examiner*—Edward M. Coven
*Assistant Examiner*—Max F. Hindenburg
*Attorney, Agent, or Firm*—Quarles & Brady

[57] ABSTRACT

A method of identifying the matching nerve fascicles in proximal and distal nerve stumps for reanastomosis comprises histochemically making a first visible image of the pattern of carbonic anhydrase emitted by the distal end of the severed nerve or its trimming and a second image of the pattern of carbonic anhydrase emitted by the proximal end of the severed nerve or its trimming, then comparing the two images and thus identifying the fascicles to be joined. A kit for preparing the images is also disclosed.

5 Claims, No Drawings

NERVE IDENTIFICATION METHOD

The present invention relates to a method of identifying the appropriate nerve fascicles in proximal and distal nerve stumps for reanastomosis and the surgical reunion of severed body parts.

BACKGROUND OF THE INVENTION

Following peripheral nerve injury in humans, fascicular reanastomosis is one method of promoting reinnervation and the return of useable function to the denervated tissues. The major factor limiting the success of this procedure has been the ability to match appropriate fascicles in the proximal and distal nerve stumps. The constancy of regional anatomical fascicular patterns, elegantly documented by Sunderland, is utilized by nerve surgeons to match fascicles (1). However, dramatic coalescence and redistribution of fascicles within a few milimeters of nerve length militates against fascicular reunion (1). Electrical stimulation testing of individual fascicles demonstrates motor and sensory responses, but the complement of sensory and motor axons in these fascicles in unknown (2). Another alternative, histochemical acetylcholinesterase staining of nerve stump biopsies distinguishes highly reactive motor axons from less reactive sensory fibers. However, the 24 to 36 hours of incubation time required for human nerves necessitates a two-stage nerve repair on separate days (3,4). At present, anatomical patterns remain the primary guides for fascicular reanastomosis.

Recently, Riley et al, discovered that carbonic anhydrase (CA) histochemistry distinguishes dorsal sensory root axons from ventral motor root axons in the rat (5,6). The presence of CA activity in sensory neurons was corroborated immunocytochemically (7).

It has been recently discovered that human peripheral nerves exhibit differential carbonic anhydrase activity and staining properties which allow for the discrimination between nerve fascicles (8, 9). The staining reaction required only 3 to 4 hours. As a result, histochemically-aided nerve repair can be accomplished in a single operation.

Nerve fascicles of human peripheral nerves can be distinguished histochemically from one another in nerve biopsies by the carbonic anhydrase staining patterns of their constituent myelinated axons (8,9). To use the staining procedure clinically would require transporting nerve biopsies from the surgery room to a histochemical laboratory for sectioning and reacting the specimens, drawing maps of the fascicular staining patterns and returning the diagrams to the surgeon for use in matching fascicles in the proximal and distal nerve stumps.

SUMMARY OF THE INVENTION

It is the primary object of the present invention to disclose a simple, dependable method of identifying the appropriate nerve fascicles in the proximal and the distal stumps of severed nerves thus facilitating reanastomosis.

It is a further object to disclose a kit for performing the above described method.

The method of the present invention comprises trimming the cut ends of the severed nerves, if necessary, histochemically making a first visible image of the pattern of carbonic anhydrase emitted by one cut end of the severed nerves and a second image of the pattern of carbonic anydrase emitted by the other cut end of the severed nerves, then comparing the two images to identify the appropriate fascicles to be joined.

An alternative method would be to use the routine necessary debridement trimmings of both cut ends to form the first and second images.

The visible images are obtained by bringing a first recording medium for carbonic anhydrase into contact with the cut end or the debridement trimming of the proximal stump and a second recording medium for carbonic anhydrase into contact with the cut end or the debridement trimming of the distal stump of the severed nerve. The medium is then allowed to be imprinted with carbonic anhydrase emitted by the cut nerve ends or trimmings to produce an identifying pattern. The pattern on the medium is then reacted with a carbonic anhydrase staining agent and the stained images thus produced on the first and second recording media compared to identify the appropriate nerve fascicles for reanastomosis. This histochemical identification of fascicles is more accurate than the current surgical practice of relying on fascicular size and distribution.

The described method is preferably performed utilizing a kit which includes as the recording medium absorbent paper upon which the carbonic anhydrase emitted from the cut nerve ends or trimmings can be absorbed. The paper can be pretreated with a binder to fix the carbonic anhydrase or a container of the binder can be included in the kit. Another component of the kit is an agent for staining the carbonic anhydrase on the paper to produce visible images of the nerve fascicles of the proximal and distal ends of the severed nerves. The preferred staining agent is that employed in the conventional carbonic anhydrase (CA) histochemical technique.

The kit provides for a more rapid (less than 1 hour), simple and on-site demonstration of fascicular patterns without histological sectioning and as such will be especially useful for surgeons not having close access to a histochemical laboratory.

These and other objects of the invention will be apparent to those skilled in the art from the description which follows:

DESCRIPTION OF THE PREFERRED EMBODIMENT

In the preferred practice of the invention the transected ends of the damaged nerves are trimmed as is standard for surgical reunion. Following trimming, one piece of recording material, preferably absorbent paper, is placed over the exposed end of the proximal nerve stump and a second is placed over the exposed end of the distal nerve stump. Alternatively, trimmings of the proximal and distal nerve cut ends are placed on absorbent paper. The recording media is kept in contact with the nerve ends or trimmings long enough to allow carbonic anhydrase from the nerves to be absorbed. The enzyme is held in position on the paper by adding a binding agent or by impregnating the paper with the binding agent prior to use. Binding agents which may be used include the preferred agents glutaraldehyde, immobilized carbonic anhydrase II antibodies, and positively or negatively charged substances such as polylysine, phosphate groups, anions or cations. After the initial binding, the carbonic anhydrase should be locked into place, if necessary, with a cross linking reagent, such as glutaraldehyde, to maintain position during incubation for carbonic anhydrase activity. The carbonic anhydrase is then stained by a cobalt ion precipitation of CA enzyme sites utilizing the modified histochemical incubation medium of Hansson (10). After a short incubation (2-8 minutes), ammonium sulfide treatment forms dark cobalt sulfide precipitates on the paper to mark the sites at which high levels of enzyme are deposited from the nerve axons. Cutaneous fascicles which contain mostly reactive axons produce more intensely stained spots than the muscular fascicles which possess fewer reactive axons thus the two fascicles can be distinguished. The fascicular imprint staining patterns on the papers bearing the carbonic anhydrase from the proximal and the distal ends provide visible images which can be read by a surgeon using a dissecting microscope, which is a presently required instrument for microneurosurgery. In addition to the comparing of the staining patterns, the surgeon also can rely upon fascicular distribution and the size of the fascicles to aid matching.

A brief description of the experimental work that led to the development of the method and kit of the present invention is set forth below.

EXPERIMENTAL METHODS

Development of a fixation technique for carbonic anhydrase

The highly soluble nature of nerve carbonic anhydrase dictates that fixation be employed to trap the enzyme. The standard method of preservation for rat nerves which we developed is intracardial perfusion of 2.5% glutaraldehyde (6). The fixed nerves are removed, cryoprotected with 30% sucrose and rapidly frozen for cryostat microtomy. Immersion fixation for preserving CA activity was tested on fresh sciatic nerves of rats to develop a technique suitable for human nerve biopsies. Acceptability was evaluated by comparing staining with the perfusion standard.

Processing human nerve biopsies for CA histochemistry

It was determined that immersion fixation in 2.5% glutaraldehyde gave satisfactory specific demonstration of CA activity in both human and rat nerves. Human nerve specimens were obtained at surgery and processed in the following manner:

Nerve biopsies were deposited by the surgeon into vials containing 15 ml of 2.5% glutaraldehyde in 0.1 M Na+-K+phosphate buffer pH 7.4 at 2° to 5° C. Samples remained in cold fixative during transport to the histochemical laboratory. After 2 hours, they were infiltrated with phosphatebuffered sucrose at 5° C. through an increasing series (10% sucrose for 20 min, 20% for 20 min and 30% for 1 hr) and quickly frozen in liquid nitrogen for cryostat microtomy at $-25°$ to $-30°$ C. Ten micrometer cross-sections were picked up on room temperature 2% gelatin-coated glass slides. After drying 5 minutes, the sections were postfixed 5 minutes on ice with 2.5% glutaraldehyde. The sections were then reacted for CA activity as described previously (6). CA activity was visualized by the formation of black CoS precipitate. Specificity of the staining reaction was checked by adding $10^{-6}$ M acetazolamide to the incubation medium to inhibit nerve CA activity (6).

Nerve biopsies obtained from human patients

Peripheral nerve samples were obtained as diagnostic specimens in conjunction with a neuropathologist from 3 male patients.

Patient No. 1. 36-years-old.

His ulnar nerve was severed by shattered glass approximately 3.5 cm proximal to the radian styloid process. Debridement trimmings, 3 to 4 mm in length, of the uneven nerve ends were taken 24 hours later during epineural nerve repair and placed in fixative.

Patient No. 2. 30-years-old.

A giant cell tumor of the scapula necessitated surgical removal of the shoulder girdle and upper extremity. No evidence of neuropathy was present in the limb before surgery. During amputation, musculocutaneous nerve specimens were removed for fixation, and the amputated limb was preserved by cooling for eventual removal of muscles for reconstructive surgery of the shoulder. Six hours later, 1 to 2 cm segments of the superficial radial, ulnar with its dorsal cutaneous branch in the forearm and median nerve at the level of the radial styloid were available for fixation.

Patient No. 3. 5-years-old.

Reconstructive surgery of his leg required a latissimus dorsi free muscle flap transplant. A diagnostic 0.5 cm specimen of the thoracodorsal nerve branch supplying the excised muscle was removed and fixed immediately following excision of the graft.

RESULTS

Carbonic anhydrase activity of rat dorsal and ventral roots

In the perfusion fixed nervous tissue of the rat, the dorsal sensory roots contained significantly more myelinated axons with CA reactive axoplasm than the accompanying ventral motor roots. Only the smaller diameter (3 to 8 $\mu$m) axons were stained in the motor roots. The sensory roots also contained reactive small axons, but the presence of stained large diameter axons (9 to 16 $\mu$m) distinguished the sensory from the motor roots. The myelin of the motor root axons stained while that of sensory axons was essentially nonstained.

Immersion fixation in 2.5% glutaraldehyde preserved CA activity of segments of fresh rat sciatic nerves comparable to that of perfusion fixation. The axoplasmic staining was blocked completely by $10^{-6}$ M acetazolamide in all cases. The inhibitor increased nonspecific staining of myelin.

Carbonic anhydrase staining of human peripheral nerves

Patient No. 1.

Ulnar nerve fascicles contained myelinated axons both with and without axoplasmic staining. Fascicles in which the large myelinated axons exhibited negative axoplasmic staining, the myelin was more reactive than in fascicles containing a mixture of large axons with stained and nonstained axoplasm. Clusters of small myelinated axons possessed both axoplasmic and myelin staining in those fascicles containing large axons with moderately stained myelin. Two fascicles from the distal nerve stump each retained their individual staining features and were easily recognized in sections of the proximal nerve stump at least 1 cm of nerve length distant.

A portion of the proximal ulnar nerve stump was reacted for CA activity. Some fascicles contained segregated groups of reactive and nonreactive axons. Comparison of staining intensities revealed that the overall activity of the distal stump was noticeably lower than that of the proximal stump.

Patient No. 2.

Axon and myelin staining patterns and intensities of the musculocutaneous nerve biopsied during limb amputation were comparable to that of the proximal ulnar nerve specimen of patient no. 1. Tissues obtained from the amputated limb after 6 hours exhibited fascicular staining patterns similar to that of the musculocutaneous nerve, but the staining intensity was markedly reduce The fascicular staining properties of identified cutaneous branches were compared with those of the mixed (muscular and cutaneous) main nerve branches. There were distinctly more axons with dark axoplasmic staining per fascicle in the radial cutaneous nerve than in the majority of fascicles in mixed branches. The dorsal cutaneous branch of the ulnar and the superficial radial nerves yielded similar results.

Patient No. 3.

The single fascicle in the thoracodorsal nerve branch contained a mixture of reactive and non-reactive axons. Myelin staining was not remarkable.

DISCUSSION

Discrimination of nerve fascicles by CA staining patterns

In this study, an immersion fixation technique was developed for human nerve biopsies which permitted the histochemical demonstration of acetazolamide-sensitive carbonic anhydrase activity in peripheral nerve axons. Staining of myelinated fibers was localized to the axoplasm and myelin sheaths in four different combinations: When the axoplasm was stained, the myelin was either stained or nonstained. When the axoplasm was not stained, the myelin was either stained or nonstained. Individual nerve fascicles were readily distinguished from one another both by the staining patterns and the intrafascicular distributions of the axons within each fascicle. Serial section analysis of a 1 cm length of nerve showed that these patterns were consistent along a 1 cm length of nerve, indicating the histochemical thechnique was of potential use for matching fascicles across gaps.

Nerve repair by fascicular reanastomosis has relied in the past largely on anatomical patterns, and consequently, has been restricted to the distal portions of peripheral nerves characterized by somewhat constant arrangements of fascicles (11). Jabaley et al. reevaluated fascicular anatomical patterns in the forearm and demonstrated that fascicles of individual nerve branches remained discrete over considerable distances with only minor interchange of fibers. They concluded that intraneural neurolysis, fascicular nerve repair, and interfascicular nerve grafting could be performed at more proximal nerve levels without significant functional damage (12). Histochemical identification of fascicles has an advantage over an anatomical approach because fascicles not separable by size and location may possess strikingly different staining patterns. Furthermore, variation in anatomical arrangements between individuals, although reportedly not frequent, would be readily detected histochemically (12). Staining nerve stump debridement trimmings could extend fascicular reanastomosis further proximally than currently practiced because it provides the means of resolving intrafascicular segregation of fibers after anatomical fusion of fascicles is completed.

Epineural repair relies upon surface landmarks of the epineurium such as blood vessels which provide clues for bringing into register matching axons. Wide gaps between cut nerve ends could change the relationship of surface markers to internal structures and lead to misalignment of fascicles. Histochemical characterization of the nerve ends directly demonstrated intraneural patterns for precise alignment.

Carbonic anhydrase activites of muscular and cutaneous nerves

A comparison of fascicular staining patterns of cutaneous nerve branches (superficial radial and dorsal ulnar) with muscular (thoracodorsal) and mixed nerves (ulnar, median and musculocutaneous) revealed that fascicles of cutaneous nerves were characterized by high percentages of axons with intense axoplasmic staining. This indicates that these reactive axons are predominantly sensory fibers as is true for the rat (5,6,7). On the other hand, some nerve branches carrying fibers destined for skeletal muscles possessed unique fascicles in which the axoplasm of the larger axons was nonstained and that of the smallest axons was stained; the myelin of all fibers was reactive. The staining pattern of these fascicles bore a striking similarity to that of the ventral motor roots of the rat (5,6). Thus, the larger axons may be alpha motor axons and the smaller axons gamma motor. We have additional information that the staining patterns characterize motor and sensory axons because preliminary results of CA staining of human thoracic dorsal and ventral roots showed staining patterns similar to that of rats. In spite of the tentative state of identification of axon types, the CA histochemical technique can aid nerve repair because it allows discrimination of fascicles beyond that of anatomical pattern. The brevity of the current histochemical technique (3-4 hrs) is compatible with a one-stage nerve repair operation. In preliminary tests of reduced fixation time and DMSO cryoprotection, we have successfully shortened the procedure to one hour.

Persistence of CA staining following injury

For a histochemical technique to be of value in nerve repair, staining must persist for 24 to 48 hours following injury to allow for the lapse of time between injury and surgical repair. Axons in the distal stump degenerate within hours following separation from the cell body (13); this process nears completion by 72 hours (1). Carbonic anhydrase activity persisted for 24 hours in the distal stump of an ulnar nerve severed in situ and in axons of an amputated limb following 6 hours of ischemia. While staining was decreased in both instances, the patterns were easily recognized and comparable to those of proximal nerve stumps. A previous report claimed that axoplasmic acetylcholinesterase activity of injured axons persisted up to 48 hours postlesion (4). Carbonic anhydrase activity should remain just as long.

Carbonic anhydrase activity is present in Schwann cell myelin. Schwann cells persist for months in the distal stump following in situ injury (1). It is possible that CA staining differences of Schwann cells persist beyond axon degeneration and will continue to provide an enzymatic marker for fascicle identification.

The results of this study indicate that histochemical CA staining of human nerve fibers can aid the surgical repair of nerves injured in situ and those severed in amputated body parts.

The return of useable function following injury of peripheral nerves depends upon the appropriate regeneration of axons to their end organs. Accurate alignment of fascicles in the proximal and distal nerve stumps is presumably essential for effective reinnervation. Routine debridement trimmings of severed nerves provide sufficient tissue for histochemistry. The staining procedure can be completed within 3 to 4 hours of receiving the tissue. Nerve fascicles are readily discriminated from one another by the individual staining patterns of their constituent axons. Axoplasmic staining is predominantly a feature of sensory fibers, and myelin staining is characteristic of skeletal motor axons. Carbonic anhydrase histochemistry provides a means of helping surgeons to accurately match fascicles in cut nerve ends to assist nerve repair and promote enhanced axon growth to end organs.

Preparation of visible carbonic anhydrase patterns

The feasibility of imprinting carbonic anhydrase onto an absorbent paper (Millipore filters) was demonstrated as follows: Fresh unfixed rat nerves were transected into short (2 mm) segments and the cut ends of the segments were placed in contact with Millipore filters (HAWP 013, pore size 0.45 um) for 1, 5, 15 and 30 minutes after which 2.5% glutaraldehyde was added to cross link enzyme to the nitrocellulose paper. The papers were reacted histochemically for carbonic anhydrase activity using Solution A (sulphuric acid, cobalt sulphate and potassium dihydrogen phosphate) mixed with Solution B (sodium bicarbonate) followed after a short incubation period (2–8 minutes) by treatment with ammonium sulfide in accord with the modified Hansson technique (6). Enzyme staining was present for all exposure times, leaving impressions of the axons within the areas of contact. The exposures of 5 and 15 minutes appeared optimal for this paper.

The preferred kit for practice of the method of the invention includes a supply of the absorbent paper, and suitable containers of a binder (2.5% glutaraldehyde aqueous solution) Solution A (sulphuric acid, cobalt sulphate and potassium dihydrogen phosphate), Solution B (sodium bicarbonate) and ammonium sulfide.

It will be readily apparent to those skilled in the art that a number of changes and modifications can be made without departing from the spirit of the present invention. Therefore, it is intended that the invention not be limited except by the claims which follow:

REFERENCES

1. Sunderland, S.: The anatomical basis of nerve repair. In, Nerve Repair and Regeneration. Ed. Jewett, D. L. and H. R. McCarroll. St. Louis, Mo. C. V. Mosby. 1980, p. 14–35.
2. Hakstian, R. W.: Funicular orientation by direct stimulation: an aid to peripheral nerve repair. J. Bone Joint Surg. 50A:1178, 1968.
3. Gruber, H. and Zenker, W.: Acetylcholinesterase: Histochemical differentiation between motor and sensory nerve fibers. Brain Res. 51:207, 1973
4. Gruber, H., Freilinger, G., Holle, J. and Mandl, H.: Identification of motor and sensory funiculi in cut nerves and their selective reunion. Brit. J. Plastic Surg. 29:70 1976.
5. Riley, D. A., Ellis, S. and Bain, J.: Carbonic anhydrase histochemistry reveals subpopulations of myelinated axons in the dorsal and ventral roots of rat spinal nerves. Soc. for Neurosci. Abstr. 7:257, 1981.
6. Riley, D. A., Ellis, S. and Bain, J.: Carbonic anhydrase activity in skeletal muscle fiber types, axons, apindles, and capillaries of rat soleus and extensor digitorum muscles. J. Histochem. Cytochem. 30:1275, 1982.
7. Wong, V., Barrett, C. P., Donati, E. J., Eng, L. F. and Guth, L.: Carbonic anhydrase activity in first-order sensory neurons of the rat. J. Histochem. Cytochem. 31:293, 1983.
8. Riley, Danny A. and David H. Lang. 1983. Carbonic anhydrase activity of human peripheral nerves. Anat. Rec. 205:162A–163A.
9. Riley, Danny A. and David H. Lang. 1983. Carbonic anhydrase activity of human peripheral nerves. A possible histochemical aid to nerve repair. J. Hand Surg. (In press).
10. Lonnerholm, G. 1980. Carbonic anhydrase in rat liver and rabbit skeletal muscle; further evidence for the specificity of the histochemical cobalt-phosphate method of Hansson, J. Histochem. Cytochem. 28:427–433.
11. Millesi, H.: Interfascicular nerve repair and secondary repair with nerve grafts. In, Nerve Repair and Regeneration. Ed. Jewett, D. L. and H. R. McCarroll. St. Louis, Mo. C. V. Mosby, 1980, p. 299-319.
12. Jabaley, M. E., Wallace, W. H. and Heckler, F. R.: Internal topography of major nerves of the forearm and hand: A current view. J. Hand Surg. 5:1, 1980.
13. Riley, D. A.: Ultrastructural evidence for axon retraction during the spontaneous elimination of polyneuronal innervation of the rat soleus muscle. J. Neurocytol. 10:425, 1981.

We claim:

1. A method of identifying the matching nerve fascicles in proximal and distal nerve stumps for reanastomosis which comprises histochemically making a first visible image of the carbonic anhydrase emitted by one severed nerve end and a second visible image of the carbonic anhydrase emitted by the other severed nerve end and comparing the two images to identify which nerve fascicles should be rejoined.

2. A method of identifying the matching nerve fascicles in proximal and distal nerve stumps for reanastomosis, said method comprising cutting the nerve ends, if necessary, to obtain trimmings, bringing a recording medium for carbonic anhydrase into contact with a first member selected from the proximal end of a severed nerve and its trimming and bringing a second recording medium for carbonic anhydrase into contact with a second member selected from the distal end of the severed nerve and its trimming, allowing both recording media to be imprinted with carbonic anhydrase emitted from the first and second members, staining the carbonic anydrase on the first and second recording media with an agent which reacts with the carbonic anhydrase to form a visible image of the severed nerve ends, and comparing the thus produced visible images on the first and second recording media to identify the appropriate nerve fascicles in the proximal and distal nerve ends for reanastomosis.

3. The method of claim 2 in which the first and second recording media are both absorbent paper.

4. The method of claim 3 in which the paper contains a binding agent which fixes the carbonic anhydrase on the paper.

5. The method of claim 4 in which the binding agent is glutaraldehyde.

* * * * *

UNITED STATES PATENT AND TRADEMARK OFFICE
CERTIFICATE OF CORRECTION

PATENT NO. : 4,552,145

DATED : November 12, 1985

INVENTOR(S) : Riley, et. al.

It is certified that error appears in the above-identified patent and that said Letters Patent is hereby corrected as shown below:

Column 1, line 3, insert the following as the first paragraph:

--This invention was made with government support under
Federal Grant NASA NCA 2-OR665-903 and NIH NS 15839-02
awarded by the National Institutes of Health.  The government
has certain rights in the invention--.

Signed and Sealed this

Twenty-fifth Day of May, 1993

Attest:

MICHAEL K. KIRK

Attesting Officer

Acting Commissioner of Patents and Trademarks